United States Patent [19]

Henley, Jr. et al.

[11] Patent Number: 5,085,216
[45] Date of Patent: Feb. 4, 1992

[54] NASOGASTRIC/NASOINTESTINAL ENTERAL FEEDING TUBE AND METHOD FOR AVOIDING TRACHEOBRONCHIAL MISPLACEMENT

[76] Inventors: Robert L. Henley, Jr., 5602 N. 22nd Dr., Phoenix, Ariz. 85015; Richard W. Weber, Jr., 7535 Ter., Kansas City, Mo. 64114

[21] Appl. No.: 685,230

[22] Filed: Apr. 12, 1991

Related U.S. Application Data

[63] Continuation-in-part of Ser. No. 384,505, Jul. 25, 1989.

[51] Int. Cl.[5] .............................................. A61M 31/00
[52] U.S. Cl. .................................... 128/636; 128/780; 604/164; 604/270
[58] Field of Search ............... 128/632, 635, 636, 768, 128/771, 780; 604/164, 170, 264, 270, 280; 116/206

[56] References Cited

U.S. PATENT DOCUMENTS

| | | | |
|---|---|---|---|
| 2,945,491 | 7/1960 | Gibbs | 128/635 |
| 3,373,735 | 3/1968 | Gallagher | 128/635 |
| 3,888,237 | 6/1975 | Mori | 128/635 |
| 4,200,110 | 4/1980 | Peterson et al. | 128/636 |
| 4,381,011 | 4/1983 | Somers | 128/635 |
| 4,632,119 | 12/1986 | Reichstein | 128/632 |
| 4,655,763 | 4/1987 | Malcolm | 604/404 |
| 4,704,111 | 11/1987 | Mess | 604/270 |

Primary Examiner—John D. Yasko
Assistant Examiner—Anthony M. Gutowski
Attorney, Agent, or Firm—Grace J. Fishel

[57] ABSTRACT

A feeding tube assembly for nasogastric and nasointestinal enteral feeding with a pH indicator carried by a stiffener used for inserting the feeding tube into a patient. After insertion of the end of feeding tube assembly into the patient but before the stiffener is withdrawn from the tube, the pH indicator is in communication with body fluids which ooze into the lumen of the tube through perforations provided along the distal end thereof. Misplacement of the end of the tube in the patient's tracheobronchial tree is ruled out by noting that the pH indicator has changed color indicating that it has contacted stomach acid.

6 Claims, 1 Drawing Sheet

NASOGASTRIC/NASOINTESTINAL ENTERAL FEEDING TUBE AND METHOD FOR AVOIDING TRACHEOBRONCHIAL MISPLACEMENT

CROSS-REFERENCE TO RELATED APPLICATIONS

This application is a continuation-in-part of abandoned application Ser. No. 07/384,505, filed July 25, 1989, for pH Indicating Feed Tube.

FIELD OF THE INVENTION

This invention relates to a method for avoiding feeding tube misplacement in a patient's tracheobronchial tree and to a feeding tube for verifying proper placement incorporating a pH indicator means which is withdrawn with the stiffening means used for inserting the feeding tube.

BACKGROUND OF THE INVENTION

When a feeding tube is inserted through a patient's nostril, there is always some chance that the end will be misdirected into his lungs instead of his stomach. Unfortunately, the patients at highest risk of having this occur are those who are critically ill such that their cough and gag reflexes are inhibited.

Various pleuropulmonary complications can arise as a result of a misplaced feeding tube, common of which are pneumonia, abscess and empyema. In some instances, no complications arise but in others, they are fatal.

With large bore enteric feeding tubes, it is possible to aspirate some of the stomach contents to confirm proper placement. The pH of the aspirated fluid is a useful indication of proper placement because gastric fluid has a low pH whereas fluid aspirated from other portions of the body, such as the pleural space or lung, has a pH much higher than that of gastric fluid. In general, gastric placement can be differentiated from respiratory placement by testing the pH of the aspirate. Gastric aspirates will be acidic (pH less than 6) as compared to tracheobronchial secretions and pleural fluid which will be alkaline (pH 7 or greater). The pH of the aspirate can be determined with a pH meter or with a pH indicator such as litmus.

With modern, small-bore, polyurethane enteric feeding tubes, however, it is not possible to aspirate fluid through the tubes because the tubes, which were designed for patient comfort and ease of insertion, collapse when sucked on. At the present time, other than for radiography, the proper placement of smallbore feeding tubes is checked by blowing air down the feeding tube and listening for bubbling in the stomach. This test is not entirely reliable even in the hands an experienced operator.

Modern small-bore feeding tubes have a plurality of spaced apart radiopaque markings or a line along the entire length which is visible under x-ray. The use of radiography provides positive evidence of proper placement in the stomach but is expensive and requires that the patient (sometimes critically ill) be transferred to a radiology department. This is particularly a hardship when the patient is in a nursing home and must be transported by ambulance for the x-ray. In the face of these difficulties, it not surprising that the proper placement of the feeding tube is frequently not verified. The incidence of misplacement in the tracheobronchial tree is unknown but anecdotal reports suggest that intrapulmonary placement of feeding tubes is an under-reported occurrence.

SUMMARY OF THE INVENTION

An important feature of the present invention is to provide a feeding tube assembly for avoiding tracheobronchial misplacement. The feeding tube assembly includes an elongated, flexible, thin walled tube which tends to collapse when a suction intended to draw fluids therethrough is placed on it. The tube has a lumen, a proximal end and a distal end with perforations along a preselected portion of the distal end. The perforations provide fluid communication from the lumen to the outside of the tube.

The feeding tube assembly also includes a removable, semi-rigid stiffening means in the lumen of the tube for stiffening the tube for nasoesophageal insertion into a patient. The stiffening means has a distal end adjacent the perforations and a proximal end extending beyond the proximal end of the tube. The proximal end of the stiffening means provides a handle means for removing the stiffening means from the lumen after the tube has been inserted in the patient's stomach.

The feeding tube assembly further includes a pH indicator means carried by the distal end of the stiffening means. The indictor means undergoes a color change in the presence of stomach acid and is removed with the stiffening means when the stiffening means is removed from the lumen.

Another important feature of the present invention is to provide a method for avoiding tracheobronchial misplacement of a feeding tube. In this method, a feeding tube assembly as described above is inserted into a patient. The stiffening means is removed from the tube. The pH indicator means is then inspected for a color change indicating that the pH indicator means contacted stomach acid and that the tube is not misplaced in the patient's tracheobronchial tree.

An important object of the present invention is to provide a feeding tube assembly and a method of use whereby the operator can determine that the tube has contacted stomach acid and that it is not misplaced in the patient's tracheobronchial tree.

Other objects and features of the invention will be in part apparent and in part pointed out hereinafter.

The invention accordingly comprises the constructions and methods hereinafter described, the scope of the invention being indicated by the subjoined claims.

BRIEF DESCRIPTION OF THE DRAWINGS

In the accompanying drawings, in which one of various possible embodiments of the invention is illustrated, corresponding reference characters refer to corresponding parts throughout the several views of the drawings and in which.

DETAILED DESCRIPTION OF THE INVENTION

Figure 1:
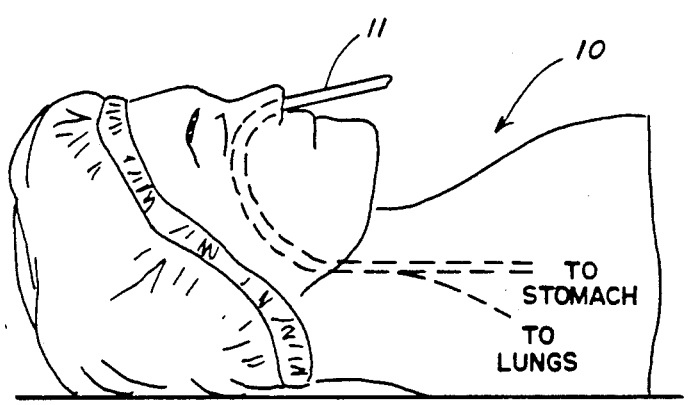
FIG. 1 illustrates the manner in which a feeding tube is inserted into the body of a patient and the fact that the tube may be diverted from the stomach into the lungs.

Referring to the drawings more particularly by reference character, FIG. 1 illustrates a patient 10 with a feeding tube assembly 11 in accordance with the present invention inserted into his stomach or intestine. Occasionally, as shown in FIG. 1, feeding tube assembly 11 is inadvertently misplaced in the patient's tracheobronchial tree which event as more particularly described below can be easily detected with feeding tube assembly 11.

Figure 2:
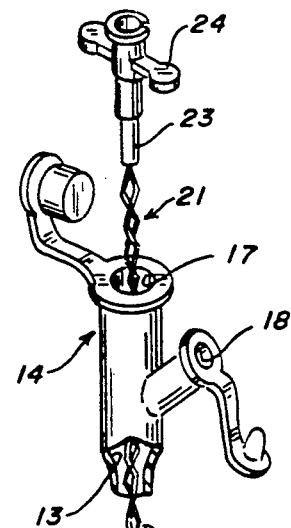
FIG. 2 is a side view of a feeding tube assembly in accordance with the present invention.
Figure 3:
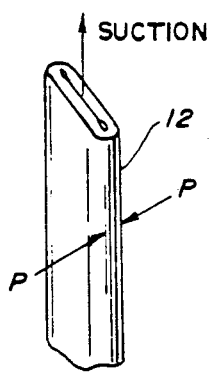
FIG. 3 illustrates the manner in which the walls of the tube collapse when subjected to the pressures induced by suction forces; and, FIG. 4 is a detail on an enlarged scale of the distal end of the feeding tube assembly with the sidewall of the tube broken away to show the pH indicator means carried by the distal end of the stiffening means.

As shown in FIG. 2, feeding tube assembly 11 includes an elongated, flexible, thin walled tube 12. Tube 12 is designed for the comfort of the patient and to facilitate insertion. As shown in FIG. 3, when a suction is applied to tube 12, the external pressure P causes tube 12 to collapse, closing the lumen and preventing the drawing of a fluid therethrough. Hence, unlike larger bore feeding tubes, fluids cannot be aspirated through tube 12 to confirm proper placement.

Figure 4:
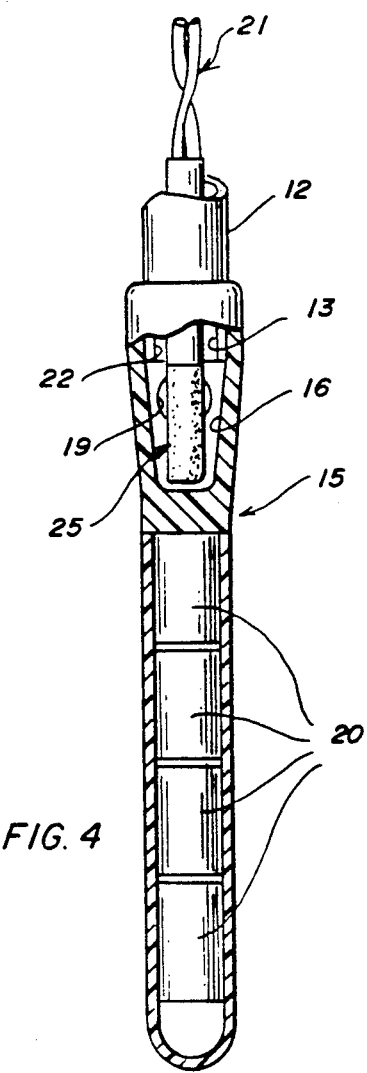

Tube 12 has a small-bore lumen 13, a proximal end 14 and a distal end 15. Distal end 15 is closed and rounded to ease the passage of the tube through the patient's nostril and on into his esophagus and stomach. As shown in FIG. 4, distal end 15 of tube 12 can be a separate part with thicker or tougher sidewalls and an internal recess 16 for receipt of the distal end of the stiffening means described below. Proximal end 14 terminates in a port 17 which remains outside of the patient through which a fluid source of nutrition can be administered. An optional medication injection port 18 may also be provided.

With continuing reference to FIG. 4, tube 12 includes perforations or openings 19 therethrough which extend along a preselected portion of distal end 15. Openings 19 provide fluid communication between lumen 13 and the outside of tube 12. An optional weight(s) 20 is positioned below openings 19 at the extreme distal end of tube 12 to facilitate the passage of the tube into the gastrointestinal tract of the patient.

Disposed in lumen 13 is a removable, semi-rigid stiffening means or stylet 21. Stiffening means 21 is sufficiently resistant to longitudinal compressive forces to aid in the passage of tube 12 as it is inserted in a patient and can be made of stainless steel, plastic and so forth. Since tube 12 may compress slightly due to the resistance encountered along the way, stiffening means 21 has a distal end 22 which terminates a safe distance short of the closed, rounded distal end 15 of tube 12 to assure that stiffening means 21 does not poke through tube 12. For additional security, the extreme distal end 22 of stiffening means 21 may be received in recess 16 provided therefore. As illustrated, distal end 22 of stiffening means 21 terminates above weight(s) 20 adjacent perforations 19. Stiffening means 21 has a proximal end 23 extending beyond proximal end 14 of tube 12. The extreme end of proximal end 23 preferably includes a handle means 24 for removing stiffening means 21 from lumen 13 after tube 12 has been inserted into the patient. The interior of lumen 13 may be lubricated to facilitate removal of stiffening means 21.

A pH indicator means 25 is carried by distal end 22 of stiffening means 21. Indicator means 25 resists detachment from stiffening means 21 in the presence of body fluids such that it is extracted from tube 12 along with stiffening means 21. Indicator means 25 is selected such that it undergoes a color change in the presence stomach acid. By way of example and not of limitation, pH indicator means 25 can be wicking which has been treated with an acid-base indicator such as litmus, methyl orange, phenol red, phenolphthalein or the like. In a preferred embodiment, indicator means 25 retains the color change when once affected despite subsequent contact with body fluids having a different pH.

A radiopaque means comprising a plurality of spaced apart radiopaque marks 26 or a line 27 along the entire length of tube 12 is optionally provided to make tube 12 visible under x-ray.

Before feeding tube assembly 11 is inserted into patient 10, the procedure is explained to the patient if possible and the length of tube 12 to be inserted is determined. This length is equal to the distance from the patient's nose to his earlobe to his xiphoid process.

The preferred nostril for insertion is determined and the patient is positioned in sitting or Fowler's position. Distal end 15 of the tube portion of feeding tube assembly 11 is directed posteriorly, aiming the weighted tip parallel to the nasal septum and the superior surface of the palate. Tube 12 should be allowed to find its own passage while advancing into the nasopharynx.

The patient is provided with a glass of water and distal end 15 of the tube portion of feeding tube assembly 11 is advanced into the pharynx as the patient swallows sips of water. This is continued until tube 12 is advanced gently through the esophagus to the predetermined length.

Upon insertion of tube 12, body fluids in the vicinity of perforations 19 ooze into lumen 13 and react with indicator means 25. To confirm proper placement in the stomach, stiffening means 21 is removed from lumen 13 by gripping proximal end 14 of tube 12 in one hand and pulling handle means 24 with the other hand. Indicator means 25 is removed with stiffening means 21. A color change in indicator means 25 indicates that tube 12 has contacted acid and is properly placed in the patient's stomach. Nasogastric enteric feeding can be safely begun through port 17 immediately. If desired, proper placement can be additionally confirmed before starting feeding by radiography, by blowing air down tube 12 and listening with a stethoscope for bubbling in the stomach, and so forth.

No color change or a weak color change in indicator means 25 indicates possible misplacement of tube 12 in the respiratory tract. Tube 12 should be withdrawn and the procedure begun again with a new feeding tube assembly 11 as soon as the patient is comfortable. If radiography is readily available, misplacement can be confirmed (or ruled out) before the tube is removed if desired. As will be readily appreciated, false negatives cause the removal of tubes which are properly placed in the stomach and true negatives avoid inadvertent feeding of fluids into the lungs. False positives, on the other hand, are not possible since the fluids in the tracheobronchial tree cannot affect a color change in indictor means 25. Hence a color change in indicator means 25 always indicates proper placement in the stomach.

For nasointestinal enteral feeding, tube 12 can be placed in the intestine by natural peristaltic action. For this, the patient is changed to a semi-Fowler's position and turned on his right side after confirming placement of tube 12 in the gastrointestinal tract. Tube 12 will advance naturally approximately two inches per hour until it reaches the desired position. To prevent further advancement, tube 12 is secured to the patient's nose and cheek with tape. Nasointestinal enteral feeding can then be started through port 17 according to physician's orders.

In view of the above, it will be seen that the several objects of the invention are achieved and other advantageous results attained. As various changes could be made in the above constructions and methods without departing from the scope of the invention, it is intended that all matter contained in the above description or shown in the accompanying drawings shall be interpreted as illustrative and not in a limiting sense.

What is claimed is:

1. A feeding tube assembly for avoiding tracheobronchial misplacement comprising:
    an elongated, flexible, thin walled tube tending to collapse when a suction intended to draw fluid therethrough is placed on it, said tube having a lumen, a proximal end and a distal end, and having perforations therethrough along a preselected portion of the distal end of said tube, said perforations providing fluid communication from said lumen to the outside of said tube;
    a removable, semi-rigid stiffening means in the lumen of said tube for stiffening the tube for nasoesophageal insertion into a patient, said means having a distal end adjacent the perforations and a proximal end extending beyond the proximal end of the tube comprising handle means for removing the stiffening means from the lumen after the tube has been inserted into the patient,
    a pH indicator means carried by the distal end of the stiffening means, said indicator means undergoing a color change in the presence of stomach acid, said indicator means being removed with the stiffening means when the stiffening means is removed from the lumen by the handle means
    whereby the operator inserting the tube into the patient and removing the stiffening means can determine that the tube has contacted stomach acid and is not misplaced in the patient's tracheobronchial tree by verifying that the pH indicator means carried by the stiffening means has undergone a color change.

2. The feeding tube assembly of claim 1 wherein the pH indicator means retains a color change once affected.

3. The feeding tube assembly of claim 1 wherein the distal end of the tube is weighted to facilitate the passage of the distal end of the feeding tube assembly into the gastrointestinal tract of the patient.

4. The feeding tube assembly of claim 3 wherein the tube has radiopaque means for visualizing the tube under x-ray.

5. A method for avoiding tracheobronchial misplacement of a feeding tube comprising:
    inserting a feeding tube assembly comprising
        an elongated, flexible, thin walled tube tending to collapse when a suction intended to draw fluid therethrough is placed on it, said tube having a lumen, a proximal end and a distal end, and having perforations therethrough along a preselected portion of the distal end of said tube, said perforations providing fluid communication from said lumen to the outside of said tube;
        a removable, semi-rigid stiffening means in the lumen of said tube for stiffening the tube for nasoesophageal insertion into a patient, said means having a distal end adjacent the perforations and a proximal end extending beyond the proximal end of the tube comprising handle means for removing the stiffening means from the lumen after the tube has been inserted in the patient's stomach or intestine,
        a pH indicator means carried by the distal end of the stiffening means, said indicator means undergoing a color change in the presence of stomach acid, said indicator means being removed with the stiffening means when the stiffening means is removed from the lumen by the handle means;
    removing the stiffening means; and,
    inspecting the pH indicator means for a color change indicating that the pH indicator contacted stomach acid and is not misplaced in the patient's tracheobronchial tree.

6. The method of claim 5 wherein the tube has a radiopaque means for visualizing the tube under x-ray and wherein proper placement of the tube in the stomach is additionally confirmed by radiography.

* * * * *